(12) United States Patent
Strasser et al.

(10) Patent No.: US 12,196,694 B2
(45) Date of Patent: Jan. 14, 2025

(54) FLAME MONITORING IN A FLASH POINT DETERMINATION OR COMBUSTION POINT DETERMINATION

(71) Applicant: ANTON PAAR PROVETEC GMBH, Blankenfelde-Mahlow (DE)

(72) Inventors: Florian Strasser, Berlin (DE); Xenia Tuaev, Berlin (DE)

(73) Assignee: ANTON PAAR PROVETEC GMBH (DE)

( * ) Notice: Subject to any disclaimer, the term of this patent is extended or adjusted under 35 U.S.C. 154(b) by 532 days.

(21) Appl. No.: 17/626,802

(22) PCT Filed: Jun. 17, 2020

(86) PCT No.: PCT/EP2020/066725
§ 371 (c)(1),
(2) Date: Jan. 12, 2022

(87) PCT Pub. No.: WO2021/018465
PCT Pub. Date: Feb. 4, 2021

(65) Prior Publication Data
US 2022/0349849 A1     Nov. 3, 2022

(30) Foreign Application Priority Data
Jul. 30, 2019   (DE) .................... 10 2019 120 512.3

(51) Int. Cl.
*G01N 25/52*     (2006.01)
*G01N 33/22*     (2006.01)

(52) U.S. Cl.
CPC .......... *G01N 25/52* (2013.01); *G01N 33/227* (2013.01)

(58) Field of Classification Search
CPC ............................ G01N 25/52; G01N 33/227
See application file for complete search history.

(56) References Cited

U.S. PATENT DOCUMENTS

| 2,823,824 A | 2/1958 | Richardson |
| 4,845,040 A | 7/1989 | Moon et al. |
| (Continued) | | |

FOREIGN PATENT DOCUMENTS

| CA | 1316800 C | 4/1993 |
| CN | 202075255 U | * 12/2011 |
| (Continued) | | |

OTHER PUBLICATIONS

Japanese Office action for Application No. 2022-502271, dated Nov. 7, 2023, 4 pages.

(Continued)

*Primary Examiner* — Mirellys Jagan
(74) *Attorney, Agent, or Firm* — Lewis Roca Rothgerber Christie LLP

(57) ABSTRACT

A device for a flash point: determination and/or combustion point determination of a liquid sample which is receivable in a container and for a flame detection is described, comprising: a container reception for receiving the container; an infrared sensor which is arranged to detect light which is generated by a flame in a region around or within the container; an evaluation system which is coupled with the infrared sensor and is configured to evaluate infrared sensor data of the infrared sensor, to indicate a fire or a burn based on the evaluation.

16 Claims, 3 Drawing Sheets

(56) References Cited

U.S. PATENT DOCUMENTS

Figure 1:
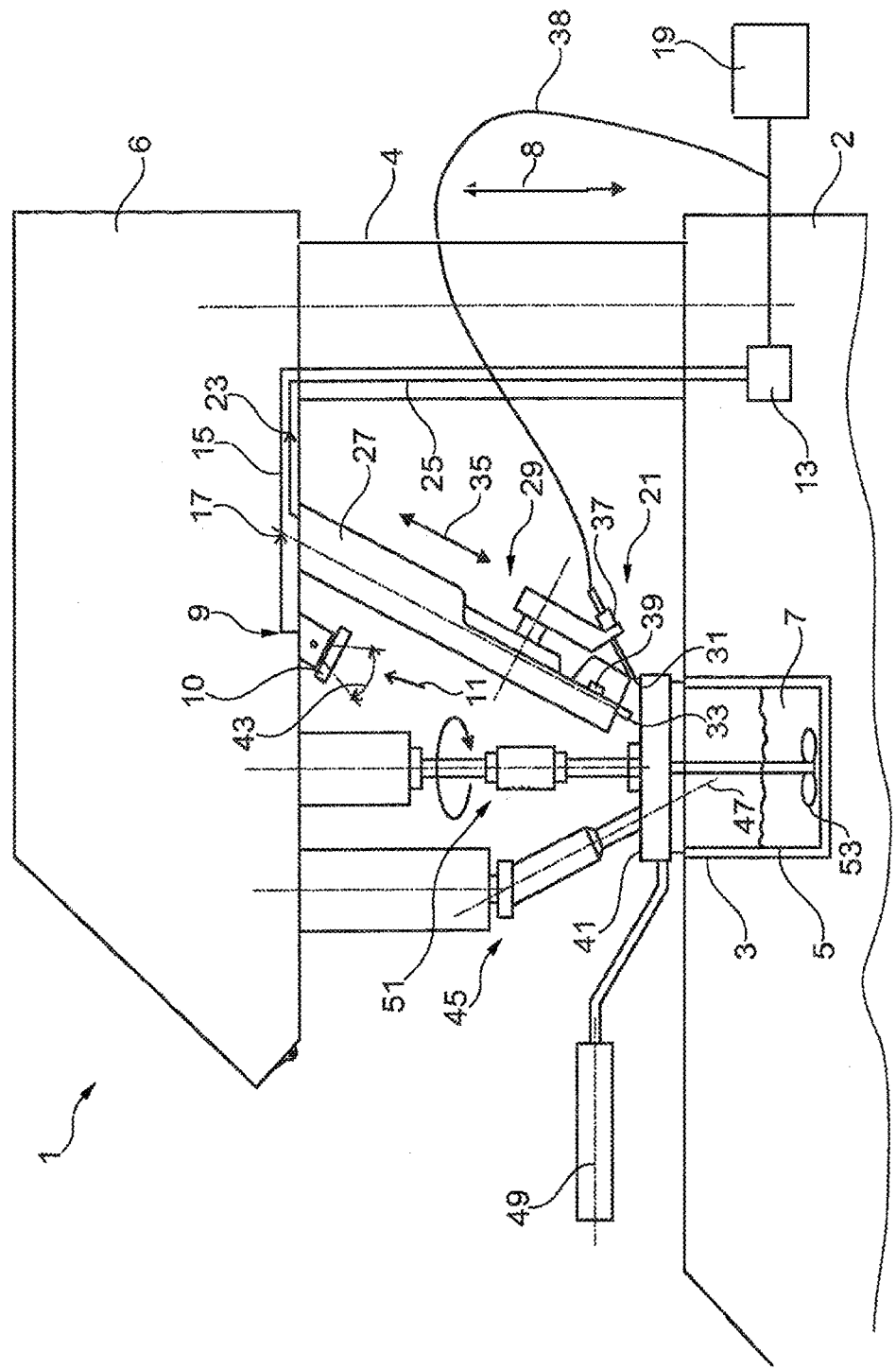

| | | | |
|---|---|---|---|
| 5,822,058 A | 10/1998 | Adler-Golden et al. | |
| 5,869,343 A * | 2/1999 | Handschuck | G01N 25/52 73/36 |
| 5,932,796 A * | 8/1999 | Arthaud | G01N 25/52 73/36 |
| 2006/0019212 A1 | 8/2006 | Chen et al. | |
| 2006/0192122 A1 | 8/2006 | Chen et al. | |
| 2008/0020479 A1 | 1/2008 | Reminiac et al. | |
| 2014/0326049 A1 | 11/2014 | Zelepouga et al. | |
| 2018/0031377 A1 | 11/2018 | Brosseau et al. | |
| 2018/0313774 A1 | 11/2018 | Brosseau et al. | |
| 2020/0096198 A1 * | 3/2020 | Williams | G01N 25/52 |

FOREIGN PATENT DOCUMENTS

| | | | | |
|---|---|---|---|---|
| DE | 1 977 206 U | | 1/1968 | |
| DE | 27 23 157 A1 | | 11/1978 | |
| DE | 29720027 U1 | * | 12/1997 | |
| DE | 196 50 302 A1 | | 6/1998 | |
| DE | 197 15 757 A1 | | 10/1998 | |
| DE | 101 21 641 A1 | | 4/2002 | |
| DE | 10206021 B4 | * | 10/2004 | G01N 25/52 |
| DE | 103 24 315 A1 | | 12/2004 | |
| EP | 2423896 A1 | * | 2/2012 | F23N 5/082 |
| JP | S55140946 U | | 10/1980 | |
| JP | S60119453 A | | 6/1985 | |
| JP | S60252249 A | * | 12/1985 | |
| JP | H06259675 A | | 9/1994 | |
| JP | H08159996 A | | 6/1996 | |
| JP | 2010216916 A | | 9/2010 | |
| KR | 10-1626281 B1 | | 6/2016 | |
| WO | WO-2020244845 A1 | * | 12/2020 | G01N 25/50 |

OTHER PUBLICATIONS

Japanese Search Report for Application No. 2022-502271, dated Oct. 10, 2023, 20 pages.
International Search Report and Written Opinion of PCT/EP2020/066725, Oct. 6, 2020, 14 pages.
German Office Action of 10 2019 120 512.3, Jun. 23, 2020, 7 pages.
German Office Action of 10 2019 120 512.3, Sep. 22, 2020, 4 pages.
Anonymous: "Herzog Optiflash Pensky Martens Easy, Safe and Accurate Flash Point Determination," https://www.optimus.de/brochures/104000.pdf, 2015, 4 pages.
Anonymous: "ShapEye 20/20R Single IR Flame Detector," https://gastech.com/files/brochures/2020R-Brochure.pdf, Jul. 2006, 2 pages.
Anonymous: "Tanaka aco-8/aco-8as Automatic Petroleum Tester," https://www.tanaka-sci.com/en/products/pdf/aco-8.pdf, Jan. 2012, 2 pages.
Heimann Sensor GmbH, "Datasheet Integrated Sensor, Type HIS Ax2 Fx Gx," http://www.sensor-ic.com, Mar. 2012, 4 pages.
Flame ionization detector—Wikipedia, https://de.wikipedia.org/wiki/Flammenionisationsdetektor, Sep. 29, 2021, 3 pages.

* cited by examiner

FLAME MONITORING IN A FLASH POINT DETERMINATION OR COMBUSTION POINT DETERMINATION

CROSS-REFERENCE TO RELATED APPLICATIONS

This application is a national US phase of PCT/EP2020/066725 which claims the benefit of the filing date of the German Patent Application No. 10 2019 120 512.3 filed 30 Jul. 2019, the disclosure of which is hereby incorporated herein by reference,

TECHNICAL FIELD

Embodiments of the present invention relate to a device for a flash point determination and/or combustion point determination of a liquid sample which is receivable in a container and for a flame monitoring. Furthermore, embodiments of the present invention relate to a method for a flame monitoring in a flash point determination and/or combustion point determination of a liquid sample which is receivable in a container.

TECHNOLOGICAL BACKGROUND

Flash point examination apparatuses are conventionally used for a characterization of combustibles (e.g. diesel, gas, kerosene, fuel oil), solvents, lubrication oils, or chemicals. According to the definition, the flash point is the lowermost temperature, at which, in an open or closed container or crucible, from the liquid to be tested under defined conditions, vapors (gaseous sample mixed with air) develop to such an extent, that a sample gas-air-mixture which is flammable by an induced ignition is formed in or outside the container.

For the determination of the flash point and/or the combustion point, preferably according to different standards, a defined amount of a sample (substance) to be tested is filled in the container (e.g. measuring crucible), heated in a controlled manner (in particular set to a predetermined temperature) and stirred, if necessary. A gaseous phase is continuously formed above the liquid sample. From a certain temperature, in periodic time distances and/or temperature distances, an ignition source is inserted in the container, to ignite the formed gas-air-sample mixture. When a flame is detected at a certain sample temperature, whose burning duration is shorter than 5 seconds, the flash point is determined. When the burning duration is longer than 5 seconds, the combustion point of the sample is determined.

For the flash point determination, different standard methods are suitable, which are substantially characterized by the methods according to i) Pensky, ii) Pensky-Martens, iii) Abel, iv) Abel-Pensky, v) Tagliabue, and vi) Cleveland.

In a flash point determination and/or combustion point determination, there is the risk of a fire of the sample. For example, the sample may be inflamed (by itself or by an igniter) and may permanently burn under flame formation. Moreover, a so-called "burn" may occur, i.e. a short-term strong unintended inflammation, when the vapor forms so fast, that in case of an ignition, a flame is generated for a short term outside or also inside the sample chamber.

In order to ensure safety in case of danger of a fire or a burn, in prior art, sensors for fire monitoring are used, for example UV sensors or temperature sensors. Typically, for a fire detection or burn detection, multiple temperature sensors have to be provided and placed, to cover a large monitoring chamber, to be able to reliably and safely detect a fire or a burn within the sample container or around the sample container. However, temperature sensors for flame monitoring and/or fire monitoring and burn monitoring have disadvantages with respect to a responding behavior, a response time, an aging, and a mechanical vulnerability.

Document DE 103 24 315 A1 discloses a method for monitoring the quality of a gas mixture which is delivered from a reformer for the operation of fuel cells. The reformate is supplied to a burner of the reformer for a determination of the quality, and the ignition of the reformate is automatically performed in the burner chamber. In dependency from the formed flame, a measuring signal is generated by a sensor, whose magnitude is evaluated for the determination of the quality of the reformate. Preferably, an ionization current signal from a flame ionization detector is evaluated for a determination of the degree of the contamination of the reformate by hydrocarbon.

Document DE 27 23 157 A1 discloses a method for detecting the flash point of an inflammable liquid to be examined, wherein the total carbon concentration value of the inflammable liquid to be examined is measured by a flame ionization detector (FID).

Document DE 197 15 757 A1 discloses a method for an operation of coal burners, wherein, for burning a certain coal, a plasma is formed by a laser beam bombardment, which is subjected to a spectrum analysis, to detect the constituents of the coal.

Document US 2014/0326049 A1 discloses a method for a real-time measurement of fuel gas compositions and heating values, wherein the measuring apparatus encompasses a near infrared sensor for measuring concentrations of hydrocarbons and carbon dioxide. A combustion is not performed.

Document U.S. Pat. No. 5,822,058 A discloses methods for optically measuring properties of hydrocarbon-fuel gases. A light source generates light at near-visible wavelengths and is transmitted through the sample. A spectrometer disperses the light which passes the sample, and a spectral image is recorded and processed.

Document DE 101 21 641 A1 discloses a method and a device for detecting the gas constitution of a natural gas, wherein the combustion gas is exposed to an infrared radiation, and wherein, for two wavelengths or spectral ranges, the portion of the infrared radiation which is absorbed by the combustion gas is captured. Therefrom, the gas constitution is determined.

Document U.S. Pat. No. 4,845,040 A discloses a method for analyzing different forms of sulfur, which are e.g. contained in coal. A mixture which contains the sample is burned within a burning zone and the burning gases are guided through an infrared analyzer which continuously monitors the intensity of the infrared spectra, From the different infrared intensity patterns, it can be concluded to the different forms of sulfur.

Document CA 1 316 800 C discloses a method for analyzing different forms of sulfur, which is similar as disclosed in the previously described document.

Document DE 196 50 302 A1 discloses a method and a device for a is determination of the gas constitution of a gas mixture, wherein the gas mixture is exposed to an infrared radiation and the portion of the infrared radiation which is absorbed by the gas mixture is measured, from which the methane number of the gas mixture is determined.

In conventional flash point testers, the flame recognition and burn recognition is performed by UV-light sensors or temperature sensors. Both types of monitoring are indeed basically suitable for the recognition of flames, but have the following impairments, for example:

The reliability of the monitoring with UV-light-sensors is depending on the environmental conditions. When the position of the measuring device is selected adversely and the measurement is performed under radiation of light with a high UV-portion, the reliability may be impaired. Additionally, using certain UV-light filtering materials (e.g. window glass) prevents a reliable detection. Since not each combustion generates the same amount of UV-light, the detection of some samples may lead to problems.

Using temperature sensors may be suboptimal due to multiple factors: i) varying/high environmental heat may lead to disturbances, ii) response velocity and sensitivity is impaired by the kind of installation: material specific coefficients of thermal conductivity and thermal conductivity resistances delimit the time of reaction, iii) a need of using multiple sensors, to cover the necessary detection area, and iv) error signals may be generated by adjacent hot parts of the measuring device (ignition approximately 1300° C., crucible lid and/or sample temperature up to 405° C.). Multiple sensors have to be placed at different locations, to differentiate a gas ignition from a fire. These sensors have to be read separately from each other, to safely recognize a fire, which renders the detection elaborate.

SUMMARY OF THE INVENTION

There may be a need to provide a device and/or a method for flame monitoring in connection with a flash point determination and/or combustion point determination, wherein a fire recognition and/or a burn recognition is reliably is enabled with a fast response time and a high safety. As a side aspect, there may be further a need to describe a method and a device for safely and reliably monitoring the presence of a flame of a gas igniter.

The subject matters of the independent claims are provided which are directed to a device and a method, respectively. The dependent claims specify special embodiments of the present invention.

According to an embodiment of the present invention, a device for a flash point determination and/or combustion point determination of a liquid sample which is receivable in a container and for a flame detection is provided, comprising a container reception for receiving the container; an infrared sensor which is arranged to detect light which is generated by a flame in a region around or within the container; and an evaluation system which is coupled with the infrared sensor and configured to evaluate signals of the infrared sensor to differentiate/detect a fire and/or a burn based on the evaluation.

Per definition, the flash point is the lowermost temperature, at which, in an open or closed crucible, from the liquid to be tested, under specified conditions, vapors develop to such an extent, that in or outside the crucible, a vapor-air-mixture is formed which is flammable by an induced ignition.

For a determination of the flash point and/or combustion point, a defined amount of a substance to be examined is filled in a container (e.g. a measuring crucible), is heated in a controlled manner and stirred, if necessary, wherein a liquid-vapor-mixture of the sample is continuously formed. In specified distances of the sample temperature change, an ignition source is inserted in the crucible, to ignite the formed liquid-vapor-mixture. If a flame is detected, whose burning duration <5 s, the flash point is detected. If the burning duration is longer than 5 s, the combustion point of the sample is determined.

The device may be suitable for a standardized flash point determination test and/or combustion point determination test which corresponds e.g. to one or more of the following standards (respectively at least for the versions which are valid at the application date): ASTM D93, DIN EN ISO 2719, GB/T261, IP 34, JIS K 2265, ISO 13736, ISO 1516, ISO 1523, DIN 51755-1 (Abel-Pensky with corresponding accessories); ASTM D56, ASTM D3934, ASTM D3941; ASTM D92, DIN EN ISO 2592, IP 36, IP 403. Embodiments may correspond to further standards which are not listed here. Embodiments of the present invention support one or more of the methods according to i) Pensky and/or ii) Pensky-Martens and/or iii) Abel and/or iv) Abel-Pensky and/or v) Tagliabue and/or vi) Cleveland. The devices according to embodiments of the present invention may correspond to the following standards: ASTM D93, EN ISO 2719, GB/T261, IP 34, JIS K2265; ASTM D92, EN ISO 2592, IP 36, IP 403, JIS K2265 (respectively at least for the versions which are valid at the application date).

For the flash point determination, different standard methods which are supported by embodiments of the present invention are suitable, which are substantially characterized by the methods according to i) Pensky, ii) Pensky-Martens, iii) Abel, iv) Abel-Pensky, v) Tagliabue and vi) Cleveland. For example, by embodiments of the present invention, the following standards for flash point testers are supported: ASTM D93, DIN EN ISO 2719, GB/T261, IP 34, JIS K 2265, ISO 13736, ISO 1516, ISO 1523, DIN 51755-1 (Abel-Pensky with corresponding accessories); ASTM D56, ASTM D3934 (flashlight/no flashlight), ASTM D3941 (equilibrium method); ASTM D92, DIN EN ISO 2592, IP 36, IP 403.

The risk of a fire of the sample is always present during a flash point measurement. As causes, e.g. an erroneous operation and/or an unknown sample composition are possible. To ensure the safety of the operator, a flash point measurement device is equipped with at least one infrared sensor (and in particular also with an FID sensor, see below) for fire monitoring. By this measure, a so-called burn may be detected in time. Burn denotes the phenomenon, when during the sample heating in the flash point measurement device, the vapor phase is formed so rapid, that in an ignition attempt, an unplanned short inflammation outside (and/or partially within) the sample chamber (i.e. container) or around the sample chamber occurs. Such a deflagration of the sample has to be detected, since the correctness of the is subsequent flash point detection cannot be ensured anymore. As a consequence, the measurement has to be stopped and restarted with a fresh sample.

The container may comprise e.g. a cylindrical shape. During the flash point determination and/or combustion point determination, the container may be partially filled, e.g. to a third or a half, with the liquid sample. The sample may be e.g. a combustible, a solvent, a lubrication oil, or other chemicals. The sample may be a mixture or a pure substance. The container reception may encompass a tempering device, to temper, in particular heat, the container and thus the sample which is received therein during the flash point determination and/or combustion point determination to a desired defined temperature. The container reception may e.g., be configured as a heating block which is made of metal and comprises an electric heater, in particular heating wires.

The infrared sensor may be installed in a fixed or variable spatial relation to the container reception. The infrared sensor may be positioned such that infrared radiation which origins from a desired monitoring region is detectable by the infrared sensor. The monitoring region may encompass a region within and/or around the container.

The flame may be a short-time flame (e.g. in case of a burn) or a continuous flame (e.g. in case of a fire). According to an embodiment of the present invention, the infrared sensor may be configured to detect both heat radiation and the presence of carbon dioxide, e.g. by detecting heat radiation in a certain spectral range. When both the presence of a heat radiation as such is detectable, and it is detectable, if and/or how much carbon dioxide is present, it may be reliably detected by the infrared sensor, if a flame (e.g. of a burn or a fire) is present in the monitoring chamber. The infrared sensor may continuously record the infrared sensor data in subsequent time intervals (e.g. for a differential measurement), to be able to determine e.g. also the time period from it, over which the flame is present.

According to embodiments of the present invention, the infrared sensor may be spatially resolving. Thus, the infrared sensor may record the total infrared is radiation which origins from the monitoring region, for example. The sensitivity of the infrared sensor may be advantageously increased. The infrared sensor may continuously perform the flame monitoring during a preparation and/or a performance and/or a post-processing of the flash point determination and/or combustion point determination, in particular with an open or closed container.

When tempering the sample and/or heating the sample, a container may be typically closed by a container lid. If the sample was e.g. erroneously too intensely heated, in case of a closed container, the sample may spontaneously inflame itself or by induced ignition, which may lead to a "burn" (which may be similar to a darting flame). Such a burn may also be generated by parts of the sample which are unintentionally spilled on parts of the device around the container and/or around the container reception. Therefore, a burn may be generated within and/or outside of the container, e.g. in case of a closed container and also in case of an open container, which may be monitored by the infrared sensor.

If a desired temperature of the sample is reached, the container lid may be opened or removed from the container, to be able to insert, in case of an open container, an ignition device into the interior of the container, to perform an ignition attempt of the sample. Also here, either a burn or a fire may be generated, wherein the fire is associated with a flame which is persistent over time. Also a fire and/or a burn in case of an open container may be monitored and detected by the infrared sensor. A fire or a burn may be indicated, e.g. by the evaluation system, due to the infrared sensor data, if the infrared sensor data exceed one or more threshold values for one or more time periods.

In an advantageous manner, the infrared sensor may be arranged spaced apart from the monitoring region, to not unnecessarily occupy space near the measuring chamber and also to reduce or even avoid a damage of the infrared sensor, e.g. by a sample gas or the flame. Furthermore, the infrared sensor may comprise a faster response time than conventionally used temperature sensors.

According to an embodiment of the invention, the infrared sensor may comprise is a region which is sensitive for heat radiation and at least one optical filter which is configured and arranged to detect at least a part of at least one absorption band of carbon dioxide from the region which is sensitive for heat radiation, The optical filter may substantially attenuate (e.g. about more than 80% or even more than 90%) e.g. wavelengths which are outside of at least one (or more) absorption band(s) of carbon dioxide, relatively to wavelengths which are within the (one or the more) absorption band(s) of carbon dioxide. In each combustion of an organic combustible which (for definition) contains carbon, carbon dioxide is partially generated. Thus, when the infrared sensor data which are detected by the infrared sensor also show a (relative) or differential concentration of carbon dioxide, it can be concluded, that the data which are detected by the infrared sensor in fact are caused by a combustion. Therefore, the infrared sensor may differentiate hot regions of the monitoring region with respect to the fact, if more or less carbon dioxide is present.

Within the monitoring region, also the container and possibly parts of the container reception may be placed, These parts of the container reception and/or the container itself are heated in a normal performance of a flash point determination and/or combustion point determination, but do not generate carbon dioxide in the heating. Due to the optical filter, the heating of the container reception and/or the container may be differentiated from a heat radiation which is generated due to a combustion. Thus, the specificity of the flame monitoring and/or the reliability of the flame monitoring may be increased, in particular the number of erroneous flame indications and/or fire indications and/or burn indications may be reduced.

According to an embodiment of the present invention, the absorption band is in a wavelength range between 4.2 μm and 4.4 μm. In other embodiments, a still further absorption band of carbon dioxide may be formed, e.g. in a range between 13 and 15 μm. In the wavelength range between 4.2 μm and 4.4 μm, carbon dioxide comprises a distinct absorption band, in which range other air constituents or gas constituents do not comprise a significant absorption band. Therefore, the specificity of the infrared sensor for proving the presence of is carbon dioxide may be improved, whereby the reliability of the flame monitoring may be increased.

According to an embodiment of the present invention, the infrared sensor comprises one or more thermal elements which define the region which is sensitive for heat radiation, and is in particular configured as a thermopile. A thermopile or thermal chain may be configured as an electric component which converts thermal energy (in particular heat radiation) to electric energy. The thermopile may consist of multiple thermal elements which are connected thermally in parallel and electrically in series, whereby the very low thermal voltages are summarized. The heat radiation may impinge on the thermal elements which are connected in series, whereby the voltage between an end of the thermal chain and another end of the thermal chain may change. Therefore, embodiments of the present invention may be implemented by conventionally available sensors.

An adjustment of the infrared sensor does not have to be necessary. It may be concluded to a fire or a burn due to a differential measurement. The change of the infrared sensor data may be used. For example, when the infrared sensor data suddenly change by an amount which is higher than a defined threshold value, it may be concluded to an inflammation. The time course of the infrared sensor signal may then provide information, if a burn or a fire is present.

According to an embodiment of the present invention, the device further comprises a flame ionization detector with two electrodes, a voltage source, to apply an electric voltage to an electrode, and an adjustable resistance measurement circuit, in particular a Wheatstone measurement circuit, to measure resistance data which indicate a resistance between the electrodes in dependency from the ionization of the air which occurs by an inflammation.

In case of a flame formation, air molecules may be ionized due to the thermal energy, whereby electrons and/or ions are released. The amount and/or the number of the electrons and/or ions may indicate a strength of the flame. In dependency of the amount and/or the concentration of the generated electrons is and/or ions, the electric resistance of the air environment (air and gaseous phase of the sample) between the two electrodes changes. When the resistance is measured by the resistance measurement circuit, it may therefore be concluded to the presence and/or the concentration of electrons and/or ions between the electrons and therefore to a flame ionization.

The two electrodes may be arranged such that a region is between them which is to be monitored by flame ionization detection. The region to be monitored by flame ionization detection may be different, in particular smaller, than the region to be monitored by the infrared sensor. The two electrodes may be arranged such that at least a region above the container reception and/or above the container may be monitored by flame ionization detection. This monitoring region may be e.g. in a space region from an upper edge of the container up to e.g., between 5 mm and 10 mm above the upper edge of the container (or the container reception).

With respect to the shapes of the two electrodes, no special limitations are required, they only have to be localized such that the region to be monitored by them is between them. In an advantageous manner, one of the electrodes may be connected to ground and a low electric voltage may be applied to the other one, e.g. between 1 Volt and 10 Volt. One or both of the electrodes may be formed by parts of a casing of the device and/or by parts of the container and/or of a container lid.

According to an embodiment of the present invention, the evaluation system is coupled with the flame ionization detector and is configured to evaluate the resistance data, wherein, based on a comparison of the measured change of the resistance with a threshold value, it is concluded to a fire or a burn and/or a gas ignition flame.

The Wheatstone measuring circuit may contain the flame ionization detector (in particular the both electrodes). The resistance circuit (Wheatstone measurement circuit) is a circuit made of two voltage dividers which are connected in parallel. The voltage between taps of the voltage dividers is measured via a voltage measuring device. When the ratio of the voltage divider resistances is equal, both taps between the voltage dividers have the same potential. A resistance of a voltage divider may be configured as variable resistance, to be able to perform an adjustment on the one hand and a measurement after the adjustment on the other hand. Both electrodes may be connected as a resistance of a voltage divider (or may be connected in parallel to another resistance).

An adjustment (in case of lack of any flame in the monitoring region) may be performed prior to each intended flash point determination and/or combustion point determination. In case of a flame formation between the electrodes, the resistance between both electrodes decreases. The variable resistance of the resistance circuit may then be readjusted, to readjust the voltage of 0 Volt between the taps of both voltage dividers, or the deflection of the point which is calibrated to zero is evaluated (deflection method). The change of the variable resistance is indicative for the degree of the ionization of the gas between the electrodes and/or the resistance between the electrodes and allows to conclude to a flame formation. Therefore, an additional independent sensor for flame monitoring is provided. The infrared sensor data and/or the resistance data may be respectively used separately or in combination for the flame monitoring. The calculation logic of the infrared sensor data and the resistance data may vary according to the application.

According to an embodiment of the present invention, the evaluation system is configured to perform a gas flame detection of a gas igniter and/or a burn detection and/or a fire detection, wherein for the fire detection and/or the burn detection both the resistance data and the infrared sensor data are used, wherein for the gas flame detection mainly the resistance data are used.

The gas flame detection of the gas igniter may be performed during a normal operation during a flash point determination and/or combustion point determination. And ignition tip of the gas igniter may be placed near to the electrodes, in particular partially between the electrodes. A burn may encompass a short-time strong inflammation (partially) within the container and/or outside is of the container. A fire may encompass a longer-lasting flame within the container or also outside of the container. When both the resistance data and the infrared sensor data are used to enable a fire detection and/or a burn detection, the reliability may be increased, in particular the number of erroneous fire detections or burn detections may be reduced.

According to an embodiment of the present invention, a fire is detected when both the resistance data and the infrared sensor data indicate an increase above respective threshold values over a minimum time period. Differential measurements may respectively be used.

According to an embodiment of the present invention, a burn is detected when both the resistance data and the infrared sensor data indicate an increase above respective threshold values for less than 1/5 or 1/10 of the minimum time for a fire. The evaluation logic may be changed according to the application and may also be adapted with respect to the parameters (threshold values, minimum time period, etc.).

According to an embodiment of the present invention, the device further comprises a container for receiving the liquid sample with a container opening.

The container may be made of metal and may be cylindrical. The container is removable from the container reception. The container opening may be circular. Therefore, conventional standardized flash point determinations and/or combustion point determinations are supported.

According to an embodiment of the present invention, the infrared sensor is arranged above the container opening, in particular in a region which is spaced apart between 5 cm and 30 cm from an upper edge of the container. Thus, the infrared sensor may be protected against damage during the measurement due to the distance, and furthermore does not have to occupy unnecessary space which is required for another measurement equipment or for handling.

In an embodiment of the present invention, the device further comprises a container lid, wherein a first one of the electrodes is formed by the container is and/or the container lid, and wherein the voltage source is configured to set the first electrode to a ground potential. The container and/or container lid may respectively fulfill a double function, to also cooperate in the flame ionization detection. When the first electrode is set to the ground potential, a danger for a user may be excluded.

According to an embodiment of the present invention, a second of the electrodes is formed by a metal part, in particular in the environment of an ignition device with at least one ignition tip which is, in particular in a straight line, displaceable into the container for igniting the sample, wherein the voltage source is configured to set the second electrode to a positive electric potential, in particular between 1 V and 10 V. Thus, in an advantageous manner, for the second electrode, no additional or separate conductive element has to be provided. Therefore, the device may be simplified. The part of the ignition device may be a part of a casing or a shell, for example. The ignition device is provided to ignite the (gaseous) sample within the container, for which purpose it is displaced into the container. When heating the sample to a next temperature value, the ignition tip may be displaced outside of the container, and the container lid may be placed on the container opening.

According to an embodiment of the present invention, the ignition device comprises an electric igniter and/or a, in particular detachable, gas igniter. Depending on the standard or a standardized test, an electric ignition and/or a gas ignition may be required. Therefore, different standards or standardized tests are supported. When the gas igniter is detachable, it may be removed, if a gas ignition is not required for the standardized test to be performed. Thereby, a manageability of the device may be improved.

According to an embodiment of the present invention, the device further comprises a temperature measuring system which is configured to measure a temperature of the sample in the liquid and/or a gaseous state within the container, to determine a flash point and/or a combustion point; and further comprises a tempering system for tempering the sample.

In particular, the tempering system may encompass an electric heater which is e.g. provided in the container reception, and wherein the container reception may be configured e.g. as a tempering block or heating block. Thus, the device is configured to perform both user defined and standardized tests for a flash point determination and/or combustion point determination.

It should be understood, that features which are described, disclosed, or applied individually or in any combination in connection with a device for a flash point determination and/or combustion point determination and for flame monitoring, are also applicable individually or in any combination to a method for flame monitoring in a flash point determination and/or combustion point determination, according to embodiments of the present invention, and vice versa.

According to an embodiment of the present invention, a method for flame monitoring in a flash point determination and/or combustion point determination of a liquid sample which is receivable in a container is provided, comprising receiving the container in a container reception; detecting light which is generated by a flame in a region around or within the container, by an infrared sensor; evaluating infrared sensor data of the infrared sensor, to indicate a fire and/or a burn, based on the evaluation.

Embodiments of the invention are now described with reference to the accompanying drawings. The embodiments are exemplary and do not delimit the scope of the invention.

DETAILED DESCRIPTION OF EXEMPLARY EMBODIMENTS

Figure 2:
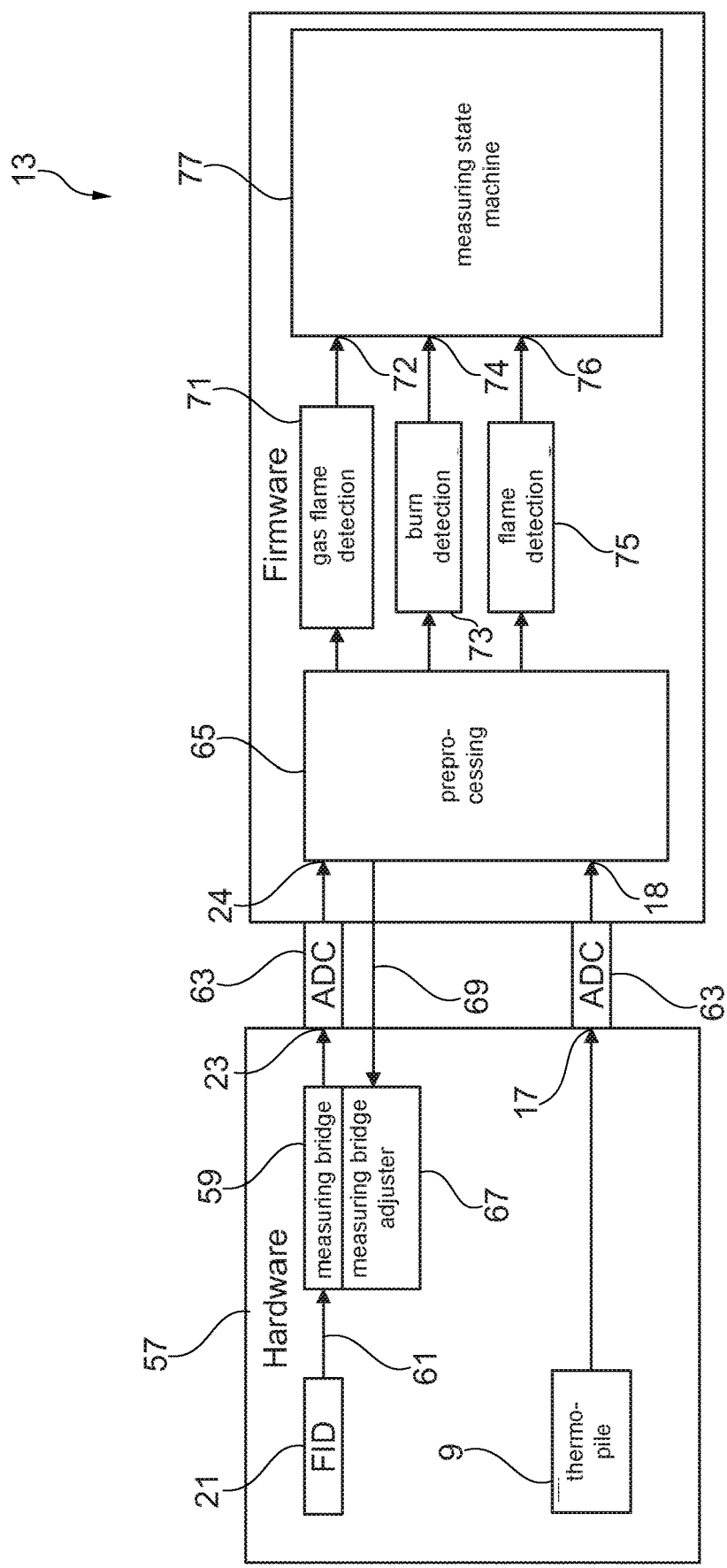
Figure 3:
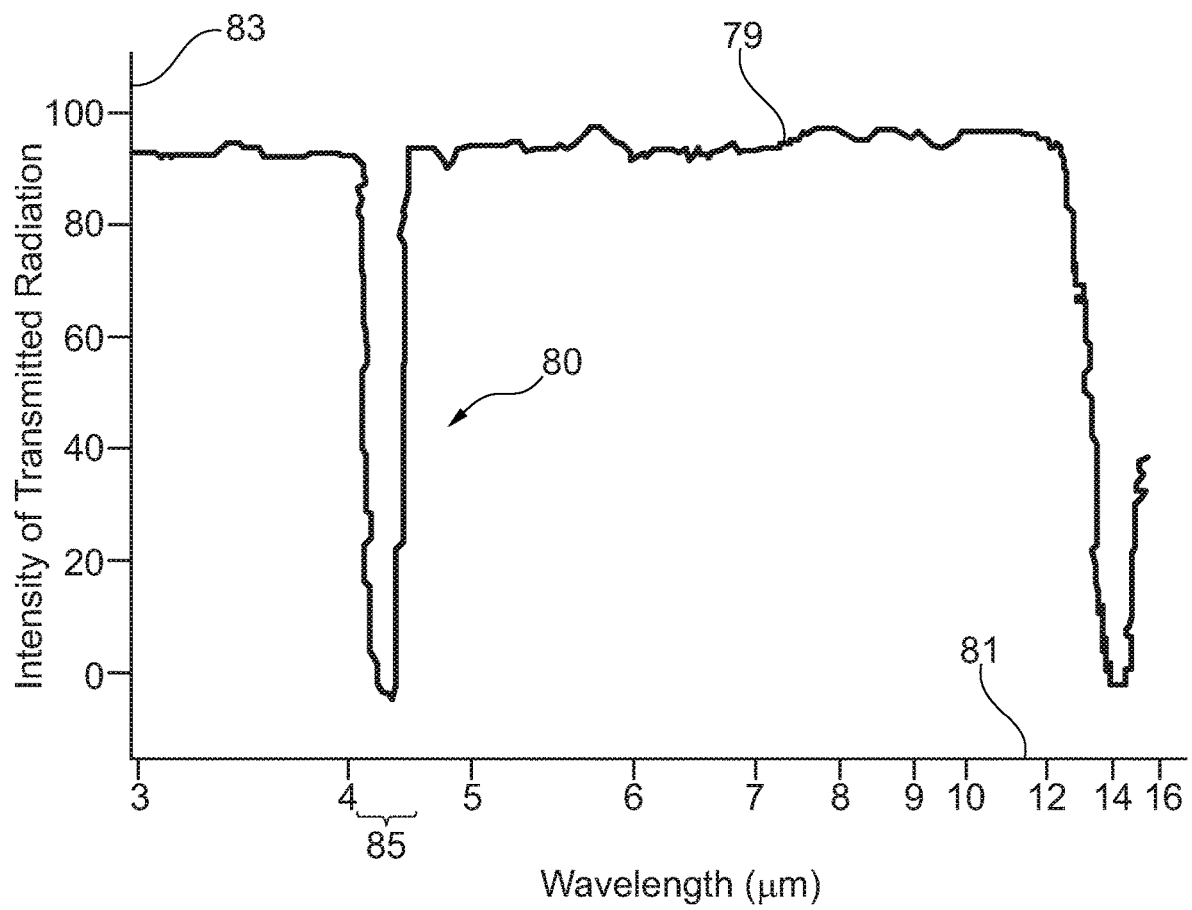

FIG. 1 illustrates in a schematic illustration a device for a flash point determination and/or combustion point determination and for flame monitoring, according to an embodiment of the present invention;

FIG. 2 schematically illustrates an evaluation system of a device for a flash point determination and/or combustion point determination and for a flame monitoring, according to an embodiment of the present invention; and FIG. 3 illustrates a transmission spectrum of carbon dioxide as it is considered by embodiments of the present invention.

The device 1 for a flash point determination and/or combustion point determination of a liquid sample which is receivable in a container and for flame monitoring according to an embodiment of the present invention, which is schematically illustrated in a side sectional view in FIG. 1, encompasses a container reception 3 for receiving a container 5. In the container 5, a liquid 7 is received. By the device 1, the flash point and/or the combustion point of the sample 7 may be determined. The device 1 further encompasses an infrared sensor 9 which is arranged to detect light 11 which is generated by a flame in a monitoring region around or within the container 5. The device 1 further encompasses an evaluation system 13 which is coupled with the infrared sensor 9 via a signal conduit 15 and is configured to obtain and evaluate infrared sensor data 17, to indicate a fire or a burn based on the evaluation, for which purpose in particular a display 19 is provided. The infrared sensor 9 encompasses an internally installed, not illustrated optical filter which is configured to selectively filter, on a region which is sensitive for heat radiation, at least a part of an absorption band of carbon dioxide, and a protection window 10.

The device 1 further encompasses a flame ionization detector 21 with two electrodes, a not illustrated voltage source, and a not illustrated adjustable resistance measurement circuit, to measure resistance data 23 which indicate a resistance between the electrodes depending on a flame ionization. The resistance data are supplied to the evaluation system 13 via a data conduit 25, and the evaluation system is configured to evaluate these resistance data 23, wherein, based on a comparison of a measured change of the resistance with a threshold value, it is concluded to a fire or a burn and/or a gas ignition flame.

A part 27 of the device 1 is configured as the second electrode of the flame ionization detector 21. The part 27 of the device also forms a casing or a shell or is holding of an ignition device 29 with at least one ignition tip 31, 33 which is displaceable into the container 5 in a straight line along a direction 35 for igniting the sample. The part 27 is made of metal and reaches at the lower end which is directed to the container 5 almost up to the ignition tips 31 and 33. The ignition tip 31 belongs to a gas igniter 37 and the ignition tip 33 belongs to an electric igniter 39. The gas igniter 37 is plugged at the shell of the electric igniter 39 and is detachable. The ignition device 21 is displaceable upwardly and downwardly along directions which are shown by the double arrow 35. The second electrode of the flame ionization detector 21 may be set to a potential between 1 V and 10 V.

The first electrode of the flame ionization detector 21 is formed by a lid 41 and/or by the container 5 and/or the container reception 3 and/or the upper surface of a base body 2. The lid and/or the container 5 and/or the container reception 3 and/or the upper surface of the base body 2 may be set to ground potential, i.e. earth potential. The flame ionization detector 21 further encompasses an adjustable resistance measurement circuit, to measure the resistance between the first electrode 41 or 5 and the second electrode 27. The resistance between both electrodes changes depending on an ionization of the molecules between the electrodes which is generated due to a flame formation.

The device 1 encompasses the base body 2 in which the container reception 3 is arranged. The container reception 3 is temperable by a tempering system. In particular, the container reception 3 may be configured as tempering block. Via a connection element 4 (e.g. an arrangement of rods or a tube), a device head 6 is connected with the base body 2. The device head may be displaced downwardly and upwardly relatively to the base body 2 along the direction 8. During a flame monitoring, the infrared sensor 9 may be spaced from an upper edge of the container 5 in a range between 5 cm and 30 cm. The infrared sensor receives light 11 from a certain angle entrance region 43 which is selected to cover a desired monitoring region.

The device 1 further encompasses a temperature sensor system 45 which is configured to measure the flash point of the sample (in particular by a is temperature measuring sensor 47) in the gaseous state and the temperature of the sample in the liquid state (by a further, not illustrated temperature measuring sensor) within the container 5, to be able to determine a flash point and/or a combustion point.

The container 5 is handable via a handle 49 by a user, to remove the container 5 from the container reception 3. The temperature measuring probe 47 reaches through an opening within the container lid 41 into the container 5. Before one of the ignition tips 31 and/or 33 is displaced along the direction 35 into the interior of the container 5, the container lid 41 is opened by a lid pusher (not illustrated) which is located on the container lid. The device 5 further encompasses a stirring device 51 with a stirrer 53 which is set into a rotational motion by a (not shown) electric motor.

The device 1 is configured to perform a method for flame monitoring in a flash point determination and/or combustion point determination according to an embodiment of the present invention.

Embodiments of the present invention use two sensors for the flame monitoring which are based on different fire monitoring principles, namely a) a flame ionization detection, and b) an optical measurement of the $CO_2$-IR-band.

The flame ionization detector (FID) 21 is based on the principle of the measurement of the resistance of the air. If a combustion of the substance occurs and a flame is generated, the observation chamber between two capacitor plates (here electrodes 27 on the one hand and 41 or 5 or 3 or the upper surface of the base body 2 on the other hand) is filled with thermally ionized steam. The electrons and/or ions which are released thereby, are caught by the capacitor plates and are recorded as a signal (e.g. 23). The response behavior of an FID for monitoring a burn is in the optimum range of some milliseconds.

The second used sensor 9 is based on the principle of substance-specific infrared (IR) transmission and absorption band(s), respectively. The is organic sample fragments and conversion products which are generated in a combustion, such as water ($H_2O$) and carbon dioxide ($CO_2$) comprise characteristic transmission bands and/or absorption bands in the IR-spectral range. In the wavelength range around 4.3 μm (wave number ~2350 $cm^{-1}$), a narrow, strongly pronounced, $CO_2$-specific peak is present, which is evaluated for the flame monitoring according to embodiments (see also FIG. 3).

Via a gas hose 38, a flammable gas is supplied to the gas igniter 37. The device 1 may further encompass a measuring procedure control, to be able to perform a flash point determination and/or combustion point determination of the sample 7 which is inserted in the container 5 according to user-defined or standardized tests.

FIG. 2 illustrates, in the larger detail, in a schematic illustration the evaluation system 13 which is illustrated in FIG. 1. The evaluation system 13 is coupled with a sensor system 57 which encompasses both the flame ionization detector 21 and the infrared detector or infrared sensor 9, here configured as "thermopile". Via a measurement bridge circuit 59, raw data 61 of the flame ionization detector 21 are transferred in the resistance data 23. The raw signals 61 of the flame ionization detector 21 are applied to the adjusted measurement bridge 59, to measure differences in the transition resistance between both electrodes 27, 41 and/or 5 and/or 3 and/or the upper surface of the base body 2. A measuring bridge adjuster 67 enables to re-adjust the measuring bridge 59 prior to each measurement. For this purpose, the measuring bridge adjuster 67 is controlled via a signal conduit 69 from the preprocessing unit 65. The signal from the infrared sensor (e.g. thermopile) 9 is already pre-amplified by a not illustrated electronics and is directly transferred as signal 17 as analog values to the converter 63. Via the analog-to-digital-converter 63, the analog resistance data 23 are converted to digital resistance data 24 and are supplied to the preprocessing unit 65 of the evaluation system 13.

The infrared sensor data 17 are also transferred via an analog-to-digital-converter 63 to corresponding digital resistance data 18 and are supplied to the preprocessing unit 65.

The evaluation unit 13 encompasses a gas flame detection module 71, a burn detection module 73, and a fire detection module 75. From the fire detection module 75 and/or the burn detection module 73, both the digital resistance data 24 and the digital infrared sensor data 18 are used. For the gas flame detection 71, (exclusively) the resistance data 24 are used. In particular, the flame ionization detector 21 according to embodiments of the present invention has the tasks of (1) burn detection and flame detection, and (2) gas flame monitoring in the crucible lid opening region.

1. Burn detection and fire detection: the burn may encompass an inflammation outside of the crucible, It may occur when the expected flash point is erroneously adjusted. The FID is especially suitable for this, since due to its short reaction time of some milliseconds, it may detect a very precise signal of such an inflammation. In case of a longer resisting flame, a fire is signalized.

2. Gas flame monitoring: the FID may be constructed such that it functions as a protective plate for the electric ignition and gas ignition at the same time. Thus, the FID is arranged very closely to the electric ignition or gas ignition (31, 33). When the gas flame is blown out by an air stream, it has to be reignited. If the gas flame is present is detected by the FID 21 by a constantly higher ionization of the air.

The single results 72, 74, 76 of the gas flame detection 71, the burn detection 73, and the fire detection 75 are supplied to a measuring state machine 77. In case of a fire detection, e.g. an extinguishing method may be initiated, after the normal measuring process was interrupted. In case of a burn detection, this may be indicated to a user and be may be asked to check the configuration data input (e.g. with respect to an expected flash point or combustion point). The detection of a gas flame which is not present may be indicated to a user, whereupon the gas flame may be reignited, e.g. by the electric igniter tip 33.

The thermopile detector 9 may perform a flame monitoring over a large surface over the measuring location and may support the FID in the decision, if a burn is is present, or if the sample contains water. In the decision, if it is a fire, a so-called voter-principle (voting principle) may be applied. When both sensors 9, 21 indicate a warning (or an indication), that a fire may be present, a (not illustrated) fire extinguishing mechanism may immediately become active. When only one sensor—either FID or thermopile—detects a fire, only after a certain time period, e.g. three seconds, the fire extinguishing becomes active.

FIG. 3 illustrates a transmission spectrum 79 of carbon dioxide in the infrared range, wherein an abscissa 81 shows the wavelength in micrometers and an ordinate 83 shows the intensity of passed radiation in percent. In a wavelength range 85, the transmission spectrum 79 shows a transmission band 80 of a reduced transmission (which corresponds to an absorption band of an increased absorption) which, according to embodiments of the present invention, selectively passes through a corresponding bandpass filter on an infrared sensor, wherein radiation of other wavelengths is substantially reduced in its intensity.

Although the device 1 which is illustrated in FIG. 1 illustrates both an infrared sensor 9 and a flame ionization detector 21, in other embodiments, the device nevertheless encompasses only an infrared detector without the need to comprise a flame ionization detector. Essential features of the device 1 are specified in the independent device claim. All other details or features in FIG. 1 and in the corresponding description are optional and may be combined in an arbitrary manner, to form further embodiments of the present invention.

The invention claimed is:

1. A device for a flash point determination and/or combustion point determination of a liquid sample which is receivable in a container and for a flame detection, comprising:
   a container reception for receiving the container;
   an infrared sensor which is arranged to detect light which is generated by a flame in a region around or within the container;
   an evaluation system which is coupled with the infrared sensor and which is configured to evaluate infrared sensor data of the infrared sensor to indicate a fire and/or a burn of the liquid sample based on the evaluation; and
   a flame ionization detector with two electrodes, a voltage source to apply an electric voltage to an electrode of the two electrodes, and an adjustable resistance measurement circuit, to measure resistance data which indicate a resistance between the electrodes depending on an ionization of the flame for evaluating the sensor data by the evaluation system.

2. The device according to claim 1, further comprising:
   a temperature measurement system which is configured to measure a temperature of the liquid sample and/or a gaseous state within the container, to determine a flash point and/or a combustion point of the liquid sample; and
   a tempering system for tempering the sample.

3. The device according to claim 1, further comprising:
   the container having a container opening for receiving the liquid sample.

4. The device according to claim 3, wherein the infrared sensor is arranged above the container opening.

5. The device according to claim 1, wherein the infrared sensor comprises a region which is sensitive for heat radiation and at least one optical filter which is configured and arranged to selectively detect at least a part of at least one absorption band of carbon dioxide from the region which is sensitive for heat radiation.

6. The device according to claim 5, wherein the at least one absorption band is in a wavelength range between 4.2 µm and 4.4 µm.

7. The device according to claim 5, wherein the infrared sensor comprises one or more thermal elements which define the region which is sensitive for heat radiation.

8. The device according to claim 1,
   wherein the adjustable resistance measurement circuit comprises a Wheatstone measurement bridge.

9. The device according to claim 8,
   wherein the evaluation system is coupled with the flame ionization detector and is configured to evaluate the resistance data wherein, based on a comparison of a measured change of the resistance with a threshold value, it is concluded to a fire or burn and/or a gas pilot flame.

10. The device according to claim 8, wherein the evaluation system is configured to perform:
    a gas flame detection of a gas igniter, and/or
    a burn detection, and/or
    a fire detection,
    wherein for the fire detection and/or the burn detection, both the resistance data and the infrared sensor data are used, and
    wherein for the gas flame detection, the resistance data are used.

11. The device according to claim 10,
    wherein a fire is detected, when both the resistance data and the infrared sensor data show an increase above respective threshold values over a minimum time period.

12. The device according to claim 11,
    wherein a burn is detected, when both the resistance data and the infrared sensor data show an increase above respective threshold values for less than 1/10 of the minimum time period.

13. The device according to claim 8, further comprising:
    a container lid,
    wherein a first of the electrodes is formed by the container and/or the container lid, and
    wherein the voltage source is configured to set the first electrode to ground potential.

14. The device according to claim 13,
    wherein a second of the electrodes is formed by a metal part having at least one ignition tip in an environmental of an ignition device, the at least one ignition tip being displaceable into the container for igniting the sample, and displaceable into the container for igniting the sample, and
    wherein the voltage source is configured to set the second electrode on a positive electric potential.

15. The device according to the preceding claim 14, wherein the ignition device comprises an electric igniter and/or a gas igniter.

16. A method for flame monitoring in a flash point determination and/or combustion point determination of a liquid sample which is receivable in a container, comprising:
    receiving the container in a container reception;
    detecting light which is generated by a flame in a region around or within the container by an infrared sensor;
    evaluating infrared sensor data of the infrared sensor to indicate a fire and/or a burn of the liquid sample, based on the evaluation; and
    using a flame ionization detector with two electrodes, a voltage source to apply an electric voltage to an electrode of the two electrodes, and an adjustable resistance measurement circuit to measure resistance data which indicate a resistance between the electrodes depending on an ionization of the flame to evaluate the infrared sensor data.

\* \* \* \* \*